US007056473B2

(12) United States Patent
Harris et al.

(10) Patent No.: US 7,056,473 B2
(45) Date of Patent: Jun. 6, 2006

(54) METHOD AND APPARATUS OF QUANTITATIVE ASSAYS

(75) Inventors: Paul C. Harris, Bothell, WA (US); Brian G. Richards, North Vancouver (CA); Jonathan G. Tippett, Vancouver (CA)

(73) Assignee: Response Biomedical Corp., Burnaby (CA)

( * ) Notice: Subject to any disclaimer, the term of this patent is extended or adjusted under 35 U.S.C. 154(b) by 0 days.

(21) Appl. No.: 10/834,447

(22) Filed: Apr. 29, 2004

(65) Prior Publication Data
US 2005/0244950 A1 Nov. 3, 2005

(51) Int. Cl.
*B32B 27/04* (2006.01)
(52) U.S. Cl. .................. 422/63; 422/100; 422/102; 422/104; 422/55; 422/58; 422/68.1; 422/215; 206/222
(58) Field of Classification Search .................. 422/63, 422/58, 56, 100–104, 50, 61, 68.1, 215, 224; 436/43, 46, 49, 174, 180; 366/130; 206/222; 435/283.1, 289.1, 290.2, 291.7
See application file for complete search history.

(56) References Cited
U.S. PATENT DOCUMENTS

| 4,340,482 | A |   | 7/1982  | Sternberg |
|-----------|---|---|---------|-----------|
| 4,618,533 | A |   | 10/1986 | Steuck |
| 5,043,265 | A |   | 8/1991  | Tanke et al. |
| 5,137,808 | A |   | 8/1992  | Ullman et al. |
| 5,304,487 | A |   | 4/1994  | Wilding et al. |
| 5,354,692 | A |   | 10/1994 | Yang et al. |
| 5,364,591 | A | * | 11/1994 | Green et al. .................. 422/58 |
| 5,498,392 | A |   | 3/1996  | Wilding et al. |
| 5,587,128 | A |   | 12/1996 | Wilding et al. |
| 5,635,358 | A |   | 6/1997  | Wilding et al. |
| 5,648,274 | A |   | 7/1997  | Chandler |
| 5,726,010 | A | * | 3/1998  | Clark ............................. 435/5 |
| 5,726,026 | A |   | 3/1998  | Wilding et al. |
| 5,869,329 | A | * | 2/1999  | Berndt ..................... 435/288.1 |
| 5,928,880 | A |   | 7/1999  | Wilding et al. |
| 6,016,712 | A |   | 1/2000  | Warden et al. |

(Continued)

OTHER PUBLICATIONS

Brown, T., "Hybridization Analysis of DNA Blots," in F.M. Ausubel et al. (eds.), *Current Protocols in Molecular Biology*, John Wiley, New York, 1998, pp. 2.10.1-2.10.16.

(Continued)

*Primary Examiner*—Long V. Le
*Assistant Examiner*—Melanie J. Yu
(74) *Attorney, Agent, or Firm*—Christensen O'Connor Johnson Kindness PLLC

(57) ABSTRACT

A sample testing apparatus (100) for use in measuring an analyte in a sample (105) is disclosed. The apparatus includes a sample well (104) for receiving the sample. A solid analyte binding agent (160) is disposed in the sample well. The apparatus further includes a mixing device (156) for mixing the sample with the solid analyte binding agent and a valve (129). The valve is configurable between a closed position for impeding flow of the sample from the sample well and an open position for releasing the sample from the sample well. The apparatus additionally includes a membrane (118) for receiving the sample once released from the sample well, the membrane having a capture reagent (164) adapted to interact with at least one of the analyte, the analyte binding agent, or a complex thereof, to aid in determining the amount of the analyte in the sample.

1 Claim, 7 Drawing Sheets

U.S. PATENT DOCUMENTS

| | | | |
|---|---|---|---|
| 6,063,589 A * | 5/2000 | Kellogg et al. | 435/24 |
| 6,184,029 B1 | 2/2001 | Wilding et al. | |
| 6,265,226 B1 * | 7/2001 | Petro et al. | 436/180 |
| 6,296,384 B1 * | 10/2001 | Yatomi et al. | 366/147 |
| 6,413,784 B1 * | 7/2002 | Lundsgaard et al. | 436/518 |
| 6,436,722 B1 | 8/2002 | Clark et al. | |
| 6,576,459 B1 | 6/2003 | Miles et al. | |
| 6,660,517 B1 | 12/2003 | Wilding et al. | |
| 6,663,833 B1 | 12/2003 | Stave et al. | |

OTHER PUBLICATIONS

Holliger, P., and H.R. Hoogenbloom, "Artificial Antibodies and Enzymes: Mimicking Nature and Beyond," *Trends in Biotechnology 13*:7-9, 1995.

Chamow, S.M., and A. Ashkenazi, "Immunoadhesins: Principles and Applications," *Trends in Biotechnology 14*:52-60, 1996.

Hayes, F.J., et al., "Simultaneous Immunoassay Using Electrochemical Detection of Metal Ion Labels," *Anal. Chem. 66:*1860-1865, 1994.

Roberts, M.A., and R.A. Durst, "Investigation of Liposome-Based Immunomigration Sensors for the Detection of Polychlorinated Biphenyls," *Anal. Chem. 67:*482-491, 1995.

Strauss, W.M., "Using DNA Fragments as Probes," in F.M. Ausubel et al. (eds.), *Current Protocols in Molecular Biology,* John Wiley, New York, 1991, pp. 6.3.2-6.3.6.

\* cited by examiner

METHOD AND APPARATUS OF QUANTITATIVE ASSAYS

FIELD OF THE INVENTION

The present invention generally relates to methods and apparatuses for performing quantitative analyses of a sample containing an analyte, and more specifically, to methods and apparatuses for performing quantitative analyses of a sample containing an analyte using an immunoassay technique.

BACKGROUND OF THE INVENTION

Quantitative analysis of cells and analytes in fluid samples, particularly bodily fluid samples and environmental samples, provides critical diagnostic and treatment information for physicians and is instrumental in detecting the presence of contaminants and bioterrorism agents in the environment. Quantitative immunoassays utilize the specificity of an antigen (Ag)—antibody (Ab) reaction to detect and quantitate the amount of an Ag or Ab in a sample. In solid phase immunoassays, one reagent (e.g., the Ag or Ab) is attached to a solid surface, facilitating separation of bound reagents or analytes from free reagents or analytes. The solid phase is exposed to a sample containing the analyte, which binds to its Ag or Ab; the extent of this binding is quantitated to provide a measure of the analyte concentration in the sample. Transduction of the binding event into a measurable signal, however, is affected by a number of limitations, including the homogeneity of the analyte and reagent in the sample and constraints of particle movement on the solid phase, which affect the specificity and applicability of quantitative immunoassays. Thus, there exists a need for a method and apparatus for performing quantitative analyses of an analyte in a fluid sample which provides a more homogeneous analyte and regent mix in the sample for enhancing the sensitivity of the quantitative analysis.

SUMMARY OF THE INVENTION

The invention relates to methods of measuring the amount of an analyte of interest in a fluid sample, using a solid phase assay (e.g., a sandwich immunoassay or an inhibition immunoassay), in which an analyte of interest and a capture reagent are used as part of a specific binding pair; and to kits for use in the methods.

In "sandwich" immunoassays of the invention, the particles are "analyte binding" particles that are coated with a binding agent (e.g., an antibody) to the analyte of interest. In "competitive" or "inhibition" assays, the particles are "analyte coated" particles that are coated with analyte of interest. In either type of assay, the particles can be labeled, using a colorimetric, fluorescent, luminescent, chemiluminescent, or other appropriate label, to facilitate detection.

In one embodiment of the methods, a fluid sample to be assessed for the analyte of interest is introduced into a sample testing apparatus. In a sandwich assay embodiment, an analyte of interest present in the sample interacts with analyte binding particles, resulting in contacted analyte binding particles within the mixed fluid sample. The buffered, mixed fluid sample is applied to an application point of a membrane strip. The membrane strip is then maintained under conditions which are sufficient to allow capillary action of fluid to transport particles to and through a sample capture zone.

The sample capture reagent interacts with contacted analyte binding particles, resulting in arrest of particles in the sample capture zone. Capillary action of the fluid further mobilizes the contacted analyte binding particles not only to and through the sample capture zone, but also to a control capture zone, where they bind to a control capture reagent. Capillary action of the fluid continues to mobilize the remaining unbound particles past the control capture zone (e.g., into a wicking pad). The amount of analyte binding particles that are arrested in the sample capture zone, and in the control capture zone, are then determined.

The amount of analyte of interest in the fluid sample is then determined. For example, the amount of analyte of interest in the fluid sample can be determined as a ratio between 1) the amount of analyte binding particles that are arrested in the sample capture zone, and 2) the amount of analyte binding particles in the control capture zone. Alternatively, the amount of analyte of interest in the fluid sample can be determined as a ratio between 1) the amount of analyte binding particles that are arrested in the sample capture zone, and 2) the sum of the amount of analyte binding particles in the control capture zone and the amount of analyte binding particles that are arrested in the sample capture zone.

In a competitive or inhibition type of assay, the mixed fluid sample is applied to the application point of the membrane strip. The membrane strip is then maintained under conditions which are sufficient to allow capillary action of fluid to transport particles to and through the sample capture zone.

The sample capture reagent interacts with analyte-coated particles; interaction of the sample capture reagent and the analyte-coated particles results in arrest of analyte-coated particles in the sample capture zone. Because of competition between the analyte-coated particles and analyte (if present) in the sample for binding sites on the sample capture reagent in the sample capture zone, the amount of analyte-coated particles arrested in the sample capture zone is inversely proportional to the amount of analyte in the sample. Capillary action of the fluid further mobilizes the analyte-coated particles not only to the sample capture zone, but also to the control capture zone, where they bind to the control capture reagent. The amount of analyte-coated particles that are arrested in the sample capture zone, and in the control capture zone, are then determined.

The amount of analyte of interest in the fluid sample is then determined. For example, the amount of analyte of interest in the fluid sample is inversely related to a ratio between 1) the amount of analyte-coated particles that are arrested in the sample capture zone, and 2) the amount of analyte-coated particles in the control capture zone. Alternatively, the amount of analyte of interest in the fluid sample is inversely related to a ratio between 1) the amount of analyte-coated particles that are arrested in the sample capture zone, and 2) the sum of the amount of analyte-coated particles in the control capture zone and the amount of analyte-coated particles that are arrested in the sample capture zone.

The flow of fluid through solid membrane strip in such quantitative assays contributes to the dynamic nature of the assays: the amount of analyte binding to particles, as well as the location of particles in relation to positions on the solid phase, is in flux. The structure of the solid phase reactants, as well as the viscosity of the fluid sample and other factors, can thereby contribute to limitations on specificity of the assays. The methods of the invention reduce certain constraints on the dynamic nature of the assays, thereby allowing more accurate determination of the amounts of analytes of interest in solutions. For example, in the sandwich assays, because the fluid sample to be assayed for the analyte of interest is mixed with the analyte binding particles prior to application to the membrane strip, there is a longer time for the analyte of interest to bind to the analyte binding particles prior to the capture reaction which occurs in the membrane strip. Furthermore, because the interaction between the analyte of interest and the analyte binding particles occurs in the fluid phase, there is faster and more efficient binding because of greater mobility of the particles, than there would be in the same interaction between analyte of interest and analyte binding particles in the matrix of the membrane strip of the solid phase apparatus. In both the sandwich assays and the inhibition (competitive) assays, it is possible to increase the volume of particles used without overloading the membrane, thereby increasing sensitivity of the assay. In addition, the particles pass over the capture zones in a continuous manner through the capillary action of the fluid, rather than in a quick wave on the crest of a fluid front, allowing more effective capture of particles and thereby enhancing sensitivity of the assays.

One embodiment of a sample testing apparatus formed in accordance with the present invention for quantitatively measuring an amount of an analyte in a fluid sample preferably using the above described methods is disclosed. The testing apparatus includes a sample well for receiving a sample containing an analyte of interest and a solid analyte binding agent disposed in the sample well. The testing apparatus further includes a mixing device moveable within the sample well to mix the sample when present in the sample well with the solid analyte binding agent. A valve is disposed in fluid communication with the sample well. The valve is configurable between a closed position for impeding flow of the sample from the sample well and an open position for releasing the sample from the sample well. The testing apparatus further includes a membrane for receiving the sample once released from the sample well, the membrane having a capture reagent disposed thereon. The capture reagent is adapted to interact with at least one of the analyte, the analyte binding agent, or a complex of analyte and analyte binding agent to aid in determining the amount of the analyte in the sample.

An alternate embodiment of a testing assembly formed in accordance with the present invention for quantitatively measuring an amount of an analyte in a fluid sample preferably using the above described methods is disclosed. The testing apparatus includes a sample well for receiving a sample containing an analyte and a mixing assembly for mixing the sample. The mixing assembly includes a mixing element moveable within the sample well between a first position and a second position to mix the sample. The mixing assembly further includes a biasing device for biasing the mixing element into the first position and an actuator assembly. The actuator assembly is used for repetitively actuating the mixing element from the first position to the second position. The biasing device moves the mixing element from the second position back into the first position.

A second alternate embodiment of a sample testing apparatus formed in accordance with the present invention for quantitatively measuring an amount of an analyte in a fluid sample preferably using the above described methods is disclosed. The testing apparatus includes a sample well for receiving a sample containing an analyte and includes a solid analyte binding agent disposed in the sample well. The testing apparatus further includes a mixing assembly having a mixing element moveable within the sample well for mixing the sample with the suspended solid analyte binding agent. The testing apparatus also includes a valve disposed in fluid communication with the sample well, the valve configurable between a closed position for impeding flow of the sample from the sample well and an open position for releasing the sample from the sample well.

One embodiment of a method performed in accordance with the present invention for determining an amount of an analyte in a fluid sample is disclosed. The method includes providing a sample well having a solid analyte binding agent disposed therein and introducing a sample into the sample well. The method further includes mixing the sample within the sample well such that the solid analyte binding agent becomes suspended in the sample forming a mixture. The method still further includes releasing the mixture upon a membrane having a capture reagent disposed thereon.

BRIEF DESCRIPTION OF THE DRAWINGS

The foregoing aspects and many of the attendant advantages of this invention will become better understood by reference to the following detailed description, when taken in conjunction with the accompanying drawings, wherein.

DETAILED DESCRIPTION OF THE PREFERRED EMBODIMENT

Figure 1:
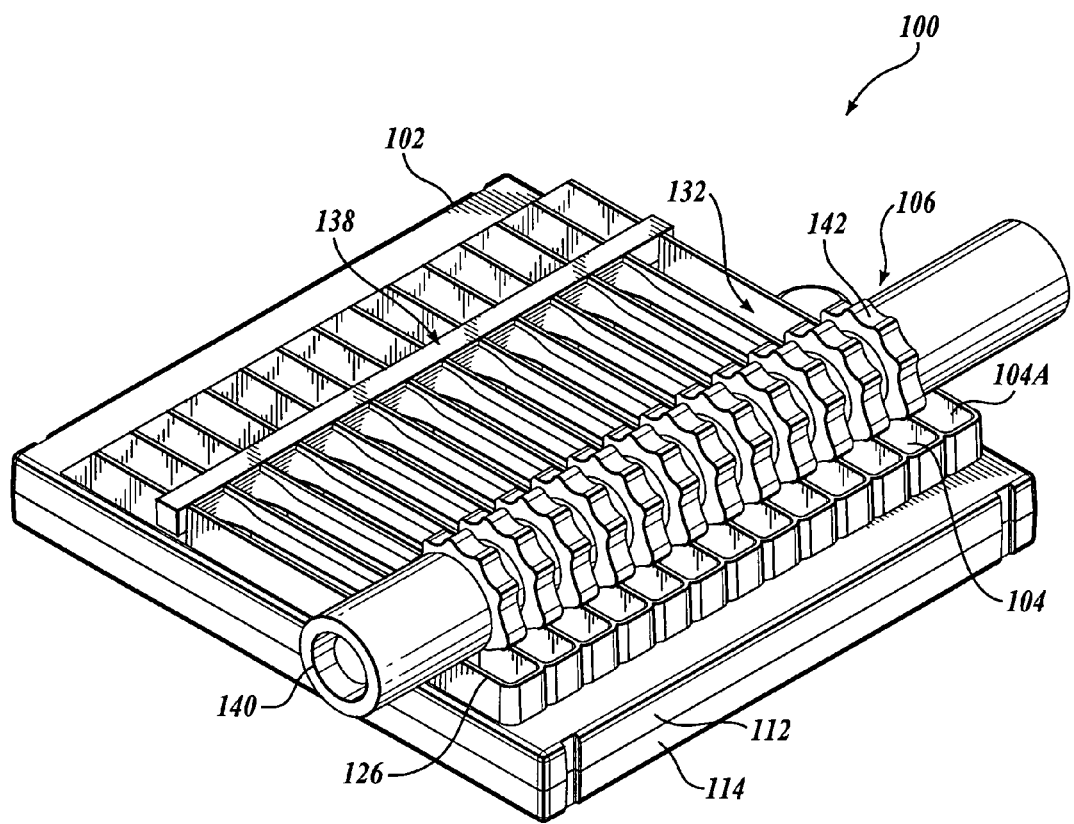
FIG. 1 is a perspective view of one embodiment of a sample testing apparatus formed in accordance with the present invention.

The present invention pertains to methods of quantitatively measuring the amount of an analyte using assays, particularly quantitative immunochromatographic assays, and kits therefor.

An "assay," as used herein, refers to an in vitro procedure for analysis of a sample to determine the presence, absence, or quantity of one or more analytes. The assays of the illustrated embodiment of the present invention utilizes an analyte and an analyte binding agent. The analyte and the analyte binding agent are members of a specific "binding pair," in which a first member of the binding pair (e.g., analyte) reacts specifically with a second member (e.g., the binding agent). One or both members of the binding pair can be an antibody. For example, a first member of the binding pair (e.g., an analyte of interest) can be an antibody, and a second member of the binding pair (e.g., a binding agent) can be an anti-immunoglobulin antibody; alternatively, the first member of the binding pair (e.g., the analyte) can be an antigen, and the second member of the binding pair (e.g., the binding agent) can be an antibody.

In one embodiment, the assay is an "immunoassay" which utilizes antibodies as a component of the procedure. In a preferred embodiment, the immunoassay is a "sandwich" assay, which is a test for an analyte in which a fluid sample to be assessed for the presence or absence, or quantity of analyte, is contacted with particles coated with an analyte binding agent, such as antibodies to the analyte, and the resultant mixture is applied to a membrane and subsequently moves by capillary action through the membrane. A positive result is indicated by detection of interaction between the analyte and analyte binding agent-coated particles in a capture zone of the membrane, the amount of analyte binding agent-coated particles in the capture zone being related to the amount of analyte in the fluid sample. In another preferred embodiment, the immunoassay is an "inhibition" or "competitive" assay, which is a test for an analyte in which a fluid test sample to be assessed for the presence or absence, or quantity of analyte, is contacted with particles coated with the analyte, and the resultant mixture is applied to a membrane and subsequently moves by capillary action the system through the membrane. A positive result is indicated by detection of interaction between analyte binding agent and analyte-coated particles in a capture zone of the membrane, the amount of analyte-coated particles in the capture zone being inversely related to the amount of analyte in the fluid sample.

In another embodiment of the assays of the invention, neither the analyte nor the binding agent are antibodies: for example, the first member of the binding pair can be a ligand, and the second member of the binding pair can be a receptor; alternatively, the first member of the binding pair can be a lectin, and the second member of the binding pair can be a sugar. In still another embodiment, the first member of the binding pair can be a nucleic acid (e.g., DNA, RNA), and the second member of the binding pair can be a nucleic acid which specifically hybridizes to the first member of the binding pair. "Specific hybridization," as used herein, refers to the ability of a first nucleic acid to hybridize to a second nucleic acid in a manner such that the first nucleic acid does not hybridize to any nucleic acid other than to the second nucleic acid (e.g., when the first nucleic acid has a higher similarity to the second nucleic acid than to any other nucleic acid in a sample wherein the hybridization is to be performed). "Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity which is less than perfect (e.g., 70%, 75%, 80%, 85%, 90%, 95%). For example, certain high stringency conditions can be used which distinguish perfectly complementary nucleic acids from those of less complementarity. "High stringency conditions", "moderate stringency conditions" and "low stringency conditions" for nucleic acid hybridizations are explained on pages 2.10.1–2.10.16 and pages 6.3.1–6.3.6 in *Current Protocols in Molecular Biology* (Ausubel, F. M. et al., "*Current Protocols in Molecular Biology*", John Wiley & Sons, (1998), the entire teachings of which are hereby incorporated by reference herein). The exact conditions which determine the stringency of hybridization depend not only on ionic strength (e.g., 0.2×SSC, 0.1×SSC), temperature (e.g., room temperature, 42° C., 68° C.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, equivalent conditions can be determined by varying one or more of these parameters while maintaining a similar degree of identity or similarity between the two nucleic acid molecules.

Regardless of the composition of the analyte and the binding agent, these two components nevertheless form a specific binding pair, in which the first member reacts specifically with the second member. Specific interaction between the members of the binding pair indicates that the first member of the binding pair preferentially binds or otherwise interacts with the second member of the binding pair, preferably to the exclusion of any binding to another compound in the assay.

The terms, "analyte" or "analyte of interest," as used herein, refer to a first member of a binding pair as described above. The analyte is a molecule or compound for which the amount will be measured. The analyte can be in the form of a solid, such as a dry substance (e.g., a powder, a particulate, spore, or other particle), or can be in the form of a fluid (e.g., a solid as described above that has been dissolved or suspended in a fluid; or other liquid sample). Examples of analytes include spores; proteins, such as hormones or enzymes; glycoproteins; peptides; small molecules; polysaccharides; antibodies; nucleic acids; drugs; toxins (e.g., environmental toxins); viruses or virus particles; bacteria; other infectious agents or products of infectious agents; portions of a cell wall; and other compounds. In a preferred embodiment, the analyte is "immunogenic," which indicates that antibodies (as described below) can be raised to the analyte, or to an analyte that is bound to a carrier (e.g., a hapten-carrier conjugate, for which antibodies can be raised to the hapten). In some representative embodiments, the analyte of interest can be myoglobin; CK-MB; troponin I; PSA; digoxin; theophylline; ricin; C-reactive protein; or b-natriuretic peptide. In other representative embodiments, the analyte of interest can be a hormone (e.g., T-3 or T-4) or a drug of abuse (LSD, THC, barbiturates, etc.). In still other representative embodiments, the analyte of interest can be an infectious agent or a product of an infectious agent, such as *Francisella tularensis* (the causative agent of tularemia); *Claustridia* or toxin produced thereby (botulinum toxin); *Variola* (smallpox) virus or other pox viruses (e.g., cowpox, monkey pox); or a spore of a type of *Bacillus*, such as *Bacillus anthracis* (anthrax) or *Bacillus globigii*. The analyte of interest can be in a liquid sample; alternatively, the analyte of interest can be in a dry (non-fluid) sample (e.g., a solid, such as a particulate sample, powder sample, or soil sample).

In the methods of the invention, a fluid sample is assessed for the presence or absence, or quantity, of an analyte of interest. The fluid can be a fluid that wets the membrane strip; that supports a reaction between the analyte of interest and the analyte binding agent, such as the antibody/antigen reaction (i.e., does not interfere with antibody/antigen interaction); and that has a viscosity that is sufficiently low to allow movement of the fluid by capillary action. In a preferred embodiment, the fluid is an aqueous solution (such as a bodily fluid). The fluid sample can be a fluid having relatively few components, for example, an aqueous solution containing the analyte of interest; alternatively, the fluid sample can be a fluid having many components, such as a complex environmental sample (e.g., sewage, waste water, groundwater, or other water sample), or a complex biological fluid (e.g., whole blood, plasma, serum, urine, cerebrospinal fluid, saliva, semen, vitreous fluid, synovial fluid, or other biological fluid). In a preferred embodiment in which the fluid is a biological fluid, the fluid is whole blood, plasma, or serum. If desired, the fluid sample can be diluted; for example, if a complex biological fluid is used as the fluid sample, it can be diluted with a solution (e.g., an aqueous solution).

If the analyte of interest is not in solution (e.g., the analyte of interest is in a dry or solid sample, as described above), it can be extracted, suspended, or dissolved into a fluid sample first. For example, if the analyte of interest is a nucleic acid, it can be extracted from cells of interest into a solution (e.g., an aqueous solution, such as the buffer described below). In another example, if the analyte of interest is a powder or particulate material (e.g., a powder, a particulate, a soil sample, or spores), it can be suspended or dissolved into a solution (e.g., an aqueous solution, such as the buffer described below) such as by obtaining a sample of the dry material (e.g., using a swab or other instrument) and placing the sample of dry material into the solution. Thus, a "fluid sample" can refer not only to a liquid sample to be assessed for an analyte of interest, but also to a fluid sample in which a solid material (to be assessed for an analyte of interest) is extracted, suspended or dissolved.

The "analyte binding agent," as used herein, refers to second member of a binding pair as described above. The analyte binding agent is a compound that specifically binds to the analyte (the first member of the binding pair), such as an antibody, a hapten or drug conjugate, a receptor, or another binding partner. In a preferred embodiment, the analyte binding agent is an antibody to the analyte of interest.

Sandwich Assays

The "sandwich" assay of the invention utilizes a solid phase apparatus. The solid phase apparatus includes a membrane strip preferably having an application point, a sample capture zone, and a control capture zone. The solid phase apparatus may optionally include a wicking pad following the control capture zone, and a sample pad adjacent to or covering the application point. The membrane strip can be made of a substance having the following characteristics: sufficient porosity to allow capillary action of fluid along its surface and through its interior; the ability to allow movement of coated particles (e.g., analyte binding particles, as described below) or complexes of particles and analyte of interest (e.g., contacted analyte binding particles, as described below) by capillary action (i.e., it must not block the particles or complexes of particles and analyte of interest); and the ability to be wet by the fluid containing the analyte (e.g., hydrophilicity for aqueous fluids, hydrophobicity for organic solvents). Hydrophobicity of a membrane can be altered to render the membrane hydrophilic for use with aqueous fluid, by processes such as those described in U.S. Pat. No. 4,340,482, or U.S. Pat. No. 4,618,533, which describe transformation of a hydrophobic surface into a hydrophilic surface. Examples of membrane substances include: cellulose, cellulose nitrate, cellulose acetate, glass fiber, nylon, polyelectrolyte ion exchange membrane, acrylic copolymer/nylon, and polyethersulfone. In a preferred embodiment, the membrane strip is made of cellulose nitrate (e.g., a cellulose nitrate membrane with a Mylar backing).

The "application point" is the position on the membrane where a fluid can be applied. An "application pad" can also optionally be used; the application pad rests on the membrane, immediately adjacent to or covering the application point. The application pad can be made of an absorbent substance which can deliver a fluid sample, when applied to the pad, to the application point on the membrane. Representative substances include cellulose, cellulose nitrate, cellulose acetate, nylon, polyelectrolyte ion exchange membrane, acrylic copolymer/nylon, polyethersulfone, or glass fibers. In one embodiment, the pad is a Hemasep®-V pad (Pall Corporation). In another embodiment, the pad is a glass fiber pad. If a wicking pad is present, it can similarly be made from such absorbent substances.

The "sample capture zone" refers to a point on the membrane strip at which a "sample capture reagent" is immobilized (e.g., coated on and/or permeated through the membrane). The sample capture reagent is an analyte binding agent, such as those described above. The sample capture reagent need not be the same analyte binding agent as described above; however, the sample capture reagent also forms a binding pair with the analyte of interest, in that it specifically and preferentially binds to the analyte of interest. In a preferred embodiment, the sample capture reagent is an antibody directed against the analyte; it can be directed against the same epitope of the analyte as, or against a different epitope of the analyte from, the epitope that binds to the antibodies used as analyte binding agents coated on the particles.

The apparatus additionally includes a "control capture reagent" immobilized in a "control capture zone." The control capture reagent is a reagent which reacts with the analyte binding particles, but which does not interact with the analyte to be measured: for example, the control capture reagent can react with the analyte binding agent on the analyte binding agent-coated particles; with another material on the particles; or with the particles themselves. For example, if the analyte binding agent is an antibody, the control capture reagent can be an anti-immunoglobulin antibody. In a preferred embodiment, the analyte binding agent is an antibody, and the control capture reagent is an anti-immunoglobulin antibody. The control capture reagent is immobilized on the membrane (coated on and/or permeated in the membrane) in a control capture zone.

The control capture zone is positioned such that the sample capture zone is between the application point and the control capture zone. In a preferred embodiment, the control capture zone is closely adjacent to the sample capture zone, so that the dynamics of the capillary action of the components of the assay are similar (e.g., essentially the same) at both the control capture zone and the sample capture zone. Although they are closely adjacent, the control capture zone and the sample capture zone are also sufficiently spaced such that the particles arrested in each zone can be quantitated individually (e.g., without cross-talk). Furthermore, in a preferred embodiment, the sample capture zone is separated from the application point by a space that is a large distance, relative to the small distance between the sample capture zone and the control capture zone. The speed of the capillary front (the border of the fluid moving through the membrane by capillary action) is inversely related to the distance of the capillary front from the application point of the fluid. Because particle capture is a rate limiting step in the assay, the distance between the contact region (where the capillary front mobilizes analyte binding particles) and the capture zones (where particles are captured) must be sufficient to retard the speed of the capillary front to a rate that is slow enough to allow capture of particles when the capillary front reaches the sample capture zone. In addition, the distance must be sufficiently large so that the total time of migration (movement of the capillary front through the entire membrane) is long enough to allow free analyte in a fluid sample to bind to analyte binding particles. The optimal distances between the components on the membrane strip can be determined and adjusted using routine experimentation.

Referring to FIG. 1, the membrane strips of the illustrated embodiment are placed in a sample testing apparatus 100. A "sample testing apparatus," as used herein, refers to an apparatus that can be used for collection of the fluid sample or into which a collected fluid sample can be deposited or stored, mixed with a reagent, and used in the performance of at least one step in conducting a quantitative assay of the fluid sample. A preferred embodiment of a sample testing apparatus 100 formed in accordance with the present invention is depicted in FIGS. 1–8.

Figure 2:
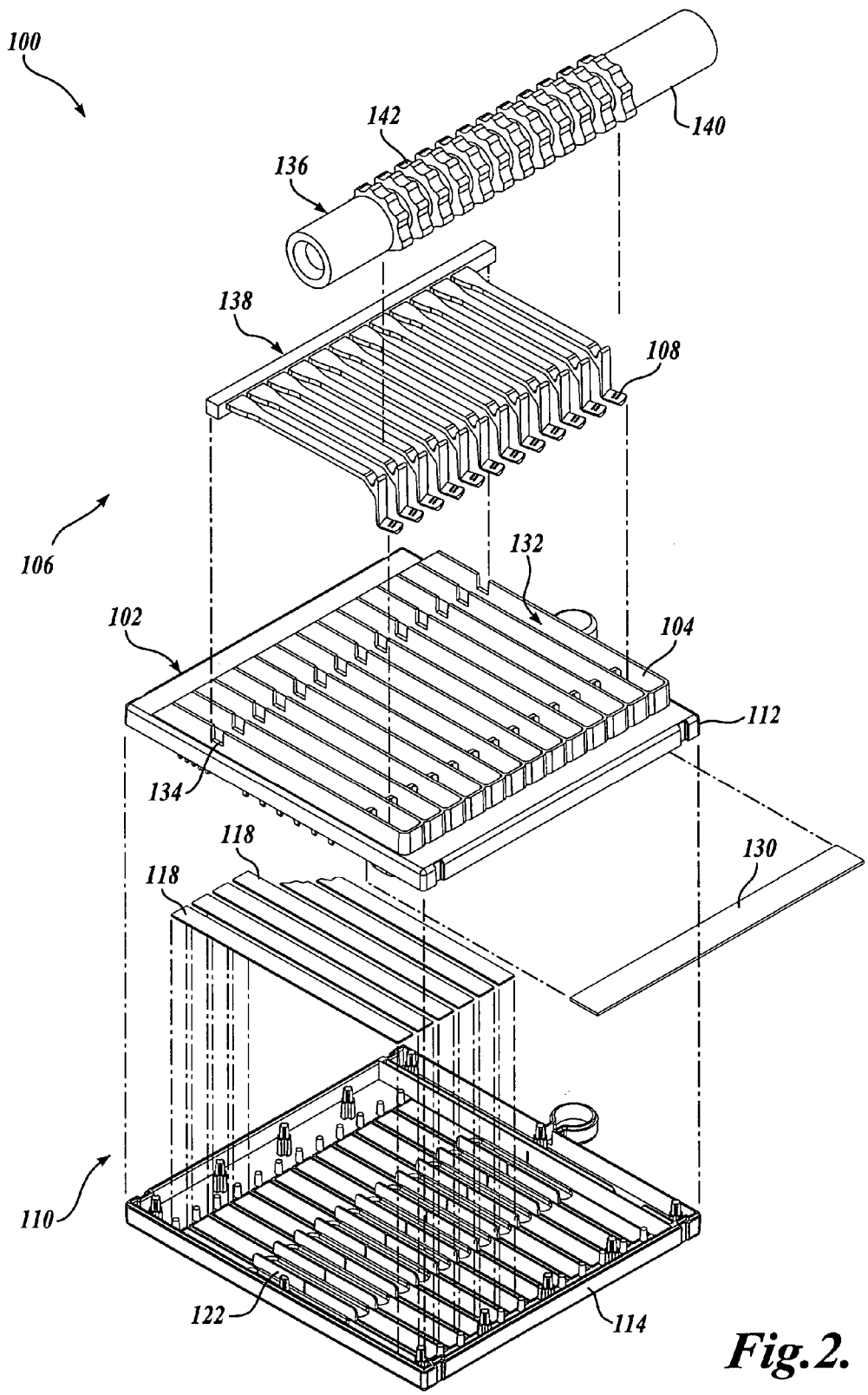
FIG. 2 is a top perspective exploded view of the sample testing apparatus of FIG. 1.

Referring to FIGS. 1 and 2, generally described, the sample testing apparatus 100 of the illustrated embodiment provides a disposable test cartridge 102 for testing a plurality of fluid samples 105 (See FIG. 6) preferably simultaneously. In this regard, the test cartridge 102 includes thirteen (13) sample wells 104 arranged in a row for receiving samples potentially having an analyte of interest. A mixing system 106 is operable to mix the samples disposed within the sample wells 104 with a reagent by reciprocating a mixing paddle 108 in each of the sample wells 104. Each of the mixed samples is then released upon a membrane strip 118 disposed within a cavity 110 of the test cartridge 102 for testing.

Figure 3:
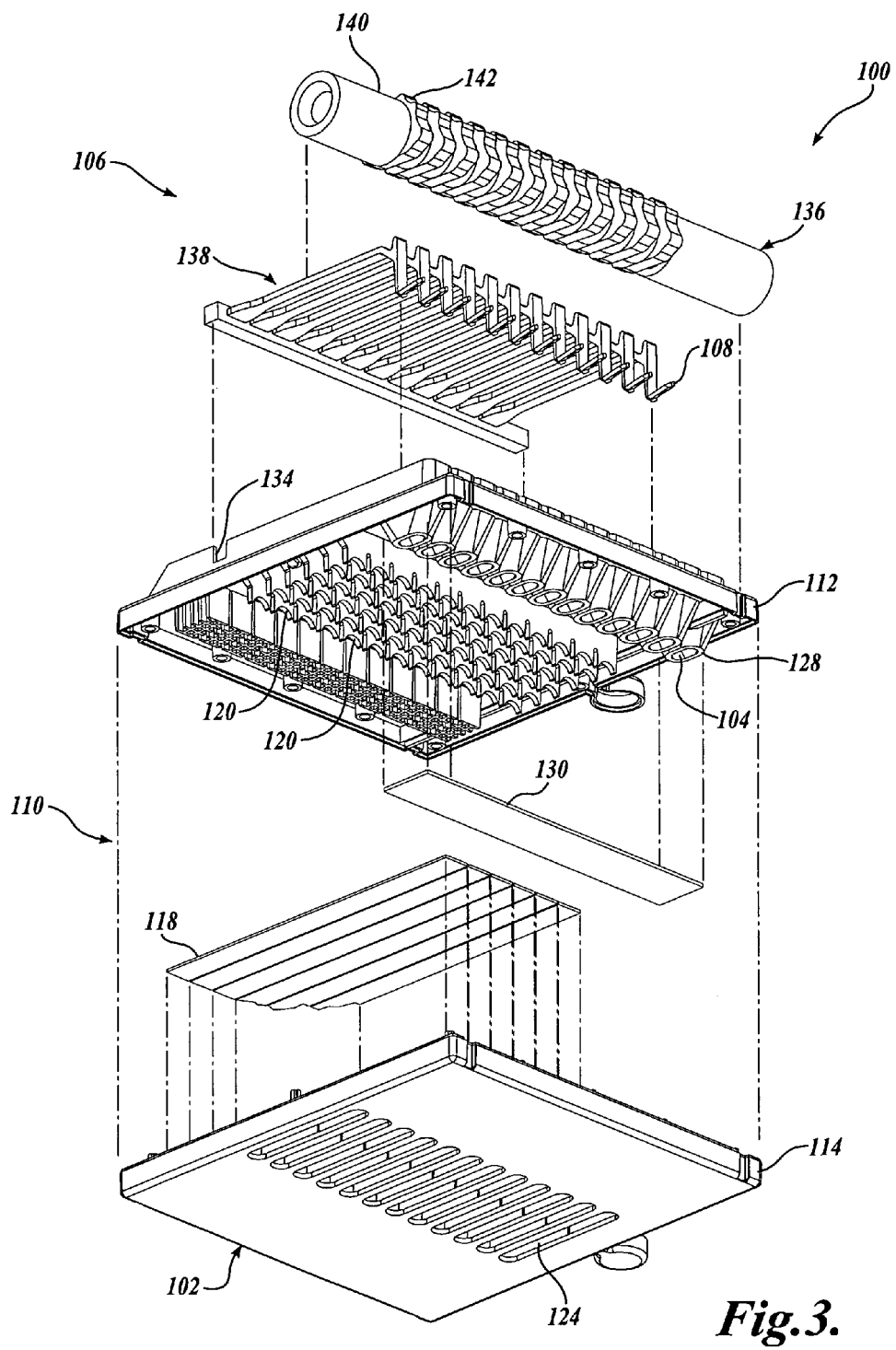
FIG. 3 is a bottom perspective exploded view of the sample testing apparatus of FIG. 1.
Figure 4:
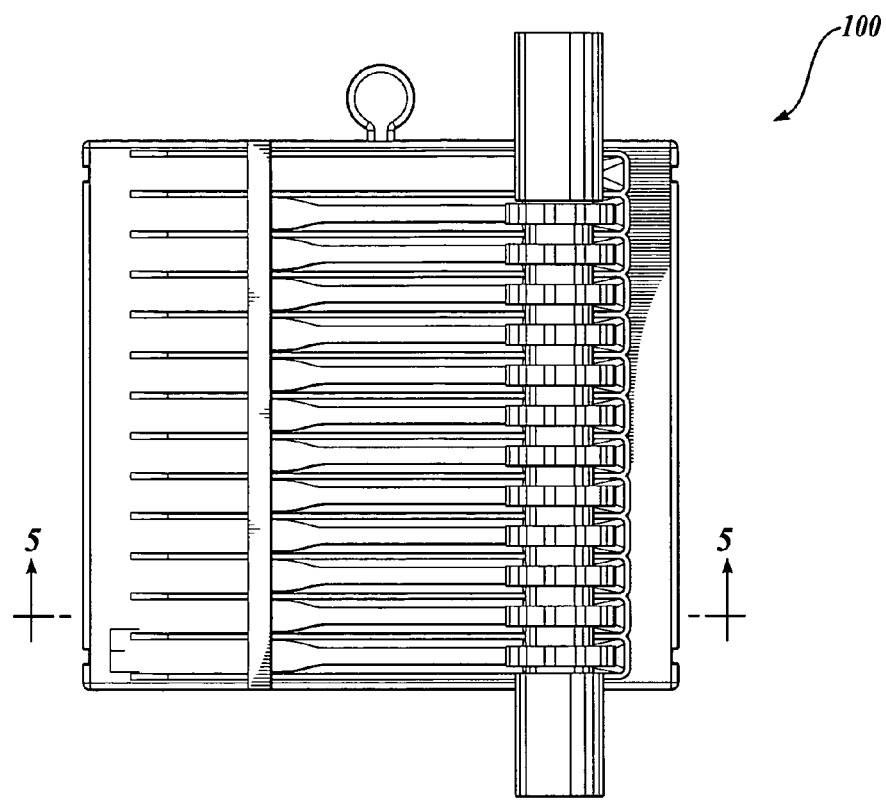
FIG. 4 is a top planar view of the sample testing apparatus of FIG. 1.

Referring to FIGS. 1–3, in light of the above general description of the sample testing apparatus 100, the structure of the sample testing apparatus 100 will now be described in greater detail. The test cartridge 102 includes an upper housing 112 and a lower housing 114 couplable to one another in a press fit arrangement. Coupling the upper and lower housings 112 and 114 to one another forms a cavity 110 there between. The cavity 110 houses twelve (12) membrane strips 118 (six shown). Each of the membrane strips 118 may be adapted to test for the presence of the same analyte, different analytes, or a combination thereof. The membrane strips 118 are oriented longitudinally along the length of the test cartridge 102 in parallel rows. The membrane strips 118 are maintained in position by a plurality of support fingers 120 projecting downward from the upper housing 112 and a plurality of side barriers 122 projecting upward from the lower housing 114.

The lower housing 114 includes a plurality of windows 124. The windows 124 are sized and configured to permit analysis of the strips 118 through the windows 124 by a suitable testing apparatus, such as by an optical based testing apparatus.

Disposed on the upper housing 112 are thirteen (13) sample wells 104. Each of the sample wells 104 is preferably funneled shaped, having a rectangular shaped top 126 and an oval shaped bottom 128. The bottoms 128 are adapted to interface with a valve 129 (see FIG. 7). The valve 129 has a closed position in which the sample 105 disposed in the sample well 104 is retained within the sample well 104 as shown in FIG. 6 and an open position in which the sample is allowed to flow from the sample well to discharge upon the membrane strips 118 as shown in FIG. 7.

Figure 6:
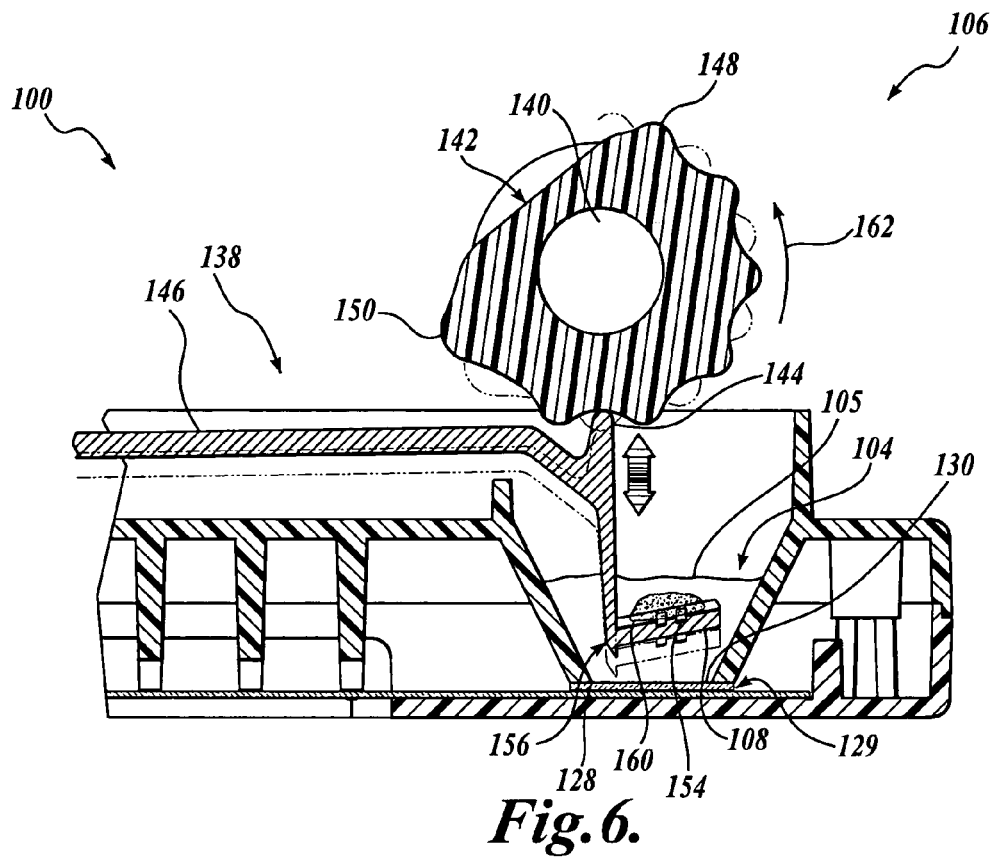
FIG. 6 is a detail view of the sample testing apparatus of FIG. 5, wherein the sample testing apparatus is depicted during a sample mixing operation.

Turning to FIG. 6, in the illustrated embodiment, each of the valves 129 is in the form of a barrier 130. To position the valve 129 in the closed position, the barrier 130 is substantially sealingly engaged with the bottoms 128 of the sample wells 104. With the barrier 130 sealingly engaging the bottoms 128, the sample wells 104 are able to receive a fluid through the open tops 126 and hold a fluid sample 105 therein.

Figure 7:
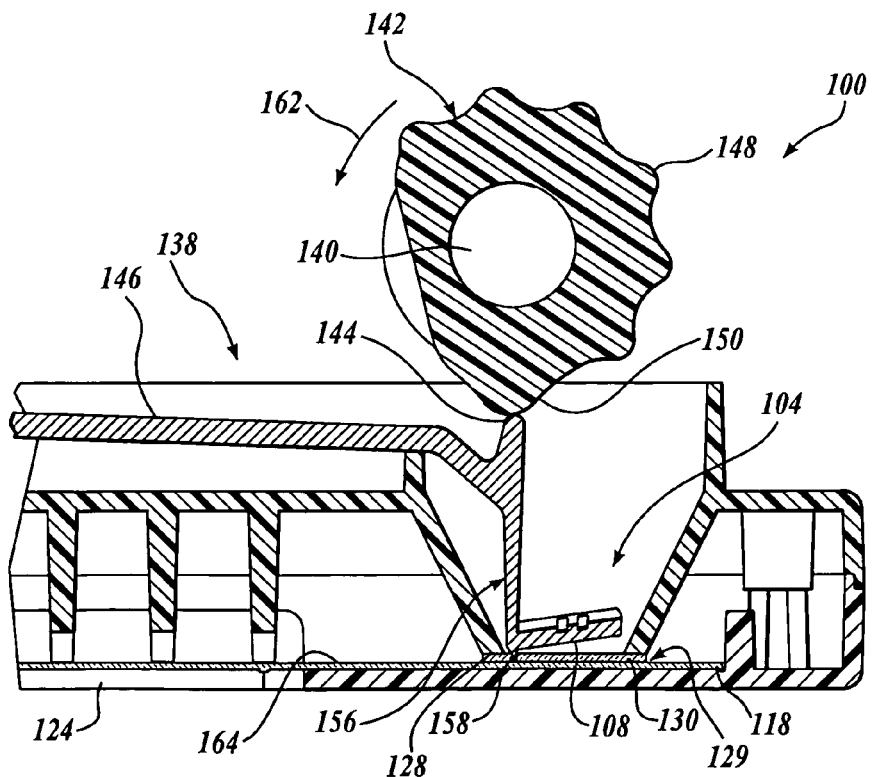
FIG. 7 is a detail view of the sample testing apparatus of FIG. 5, wherein the sample testing apparatus is depicted during a sample release operation.

Referring to FIG. 7, to position the valve 129 in the open position, the barrier 130 is partially or fully removed, or an aperture is formed in the barrier 130, such as by piercing or puncturing the barrier 130 as shown. The bottoms 128 are each disposed over one of the membrane strips 118, so that upon forming an aperture in the barrier 130, or partial or total removal of the barrier 130, each of the sample wells 104 will discharge their contents upon one of the membrane strips 118. The barrier 130 is preferably relatively inert so as not to interfere with the testing process. The barrier 130 may be attached to the open ends 128 of the sample wells 104 by any suitable means, one suitable example being by adhesive. In one working embodiment, the barrier 130 is formed from a strip of tape adhered to the bottoms 128, one example of suitable tape being invisible tape. Although the illustrated embodiment of the valve 129 is depicted and described as a barrier valve, it should be apparent to those skilled in the art that other forms of the valve 129 are suitable for use with and within the spirit and scope of the present invention, a few suitable examples being manual or automated mechanical valves, such as gate and ball valves, as well as the embodiments described below with reference to the alternate embodiment depicted in FIG. 9.

Immediately aft of each of the sample wells 104 is a longitudinally aligned channel 132. Disposed laterally across the channels 132 are a series of notches 134. The channels 132 and notches 134 are adapted to receive some of the components of the mixing system 106 as will be described in more detail below.

Turning to FIGS. 1 and 2, the mixing system 106 includes a cam assembly 136 and a cam follower assembly 138. The cam assembly 136 includes a rotatable shaft 140, the shaft having twelve (12) cams 142 circumferentially disposed upon the shaft 140. Referring now to FIGS. 4–7, each cam 142 includes seven (7) lobes. Six (6) of the lobes are of a first height forming mixing lobes 148, while the seventh lobe is of a greater height forming a puncture lobe 150, the importance of which will be discussed in greater detail below.

Each of the cams 142 are adapted to engage a cam follower 144 of the cam follower assembly 138. Each of the cam followers 144 are coupled to a distal end of a cantilever spring 146. Each of the cantilever springs 146 are coupled to a base 152 extending laterally across the test cartridge 102. The base 152 and attached cantilever springs 146 are then attached to the upper housing 112 such that the base 152 and cantilever springs 146 are received by the notches 134 and channels 132 respectively in the upper housing 112. The cantilever springs 146 bias the cam followers 144 toward the cams 142.

Of note, there are twelve (12) cam followers 144 and thirteen (13) sample wells 104. Thus, one of the sample wells 104 does not interact with the mixing system 106 and therefore, the sample held therein does not become mixed. The non-mixed sample well is referred to as the additional sample well 104A for the purposes of this detailed description. The additional sample well 104A may be used to receive a laboratory verification sample. For instance, in one working embodiment, the additional sample well 104A is used to receive a fluid sample preferably without the analyte binding particles and analyte binding agent complex 160 (See FIG. 6) suspended therein. The verification sample may then be released upon an absorbent pad (instead of upon a membrane strip 118) for holding the verification sample. The absorbent pad holds the verification sample for later laboratory verification testing of the verification sample to confirm the accuracy of the membrane strips 118 in determining the absence, presence, or quantity of the analyte of interest in the sample.

Figure 8:
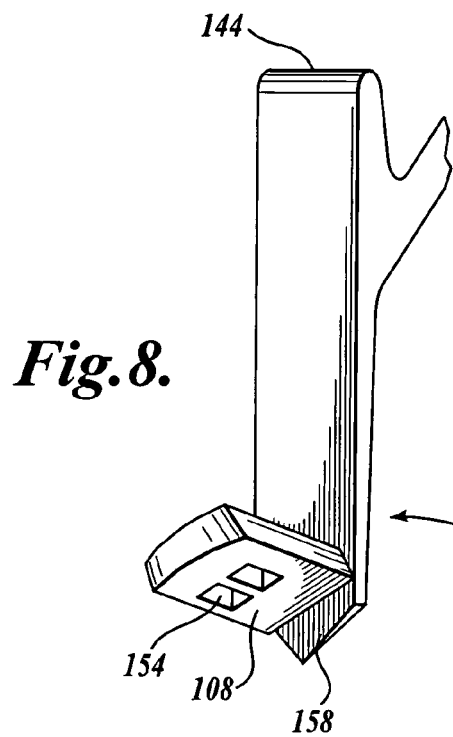
FIG. 8 is a detail perspective view of a cam follower and a mixing element of the sample testing apparatus of FIG. 1.

Turning to FIGS. 7 and 8, coupled to each of the cam followers 144 is a mixing element 156 including a mixing paddle 108. The mixing paddle 108 is a substantially rectangular panel coupled to an end of the cam follower 144. The mixing paddle 108 is inclined relative to both a lateral and longitudinal centerline of the sample testing apparatus 100. Inclining of the mixing paddle 108 causes the mixing paddle to be inclined relative to the direction of movement of the mixing paddle 108 during mixing operations, which is thought to increase the effectiveness of the mixing paddle 108.

The mixing paddle 108 further includes a pair of interwoven beams forming a complex 160 (See FIG. 6), may be placed upon the lattice 154 as a liquid. Surface tension holds the liquid reagent in place upon the lattice 154 until the reagent dries upon the lattice 154.

The mixing element 156 further includes a puncture spike 158. The puncture spike 158 projects downward from the mixing paddle 108 and is used to pierce the barrier 130 as best seen in FIG. 7, forming an aperture in the barrier 130. The aperture allows the fluid sample to flow from the sample well 104 to be absorbed by the membrane strip 118. Although a single pyramid shaped spike 158 is illustrated and described, it should be apparent to those skilled in the art that other quantities of spikes and other shapes of puncture devices are suitable for use with and within the spirit and scope of the present invention, one suitable example being a plurality of spikes.

Referring to FIGS. 1 and 2, and in light of the above description of the structure of the sample testing apparatus 100, the operation of the sample testing apparatus 100 will now be described. The sample testing apparatus 100 contains a population of "analyte binding particles" which are coated with the analyte binding agent. The population of particles varies, depending on the size and composition of the particles, the composition of the membrane strip 118 of the solid phase apparatus, and the level of sensitivity of the assay. The population typically ranges approximately between $1 \times 10^3$ and $1 \times 10^9$, although fewer or more can be used if desired. In a preferred embodiment, the population is approximately $2 \times 10^8$ particles.

The analyte binding particles are particles which can be coated with the analyte binding agent (the second member of the binding pair). In a preferred embodiment, the analyte binding particles are liposomes, colloidal gold, organic polymer latex particles, inorganic fluorescent particles or phosphorescent particles. In a particularly preferred embodiment, the particles are polystyrene latex beads, and most particularly, polystyrene latex beads that have been prepared in the absence of surfactant, such as surfactant-free Superactive Uniform Aldehyde/Sulfate Latexes (Interfacial Dynamics Corp., Portland, Oreg.).

The size of the particles is related to porosity of the membrane (for analytes in fluid samples) and also to the size of the analyte of interest (e.g., for particulate analytes): the particles must be sufficiently small to be transported along the membrane by capillary action of fluid, and also (for solid, e.g., particulate analytes, sufficiently small for the complex of contacted analyte binding particles, as described below, to be transported along the membrane by capillary action). The particles can be labeled to facilitate detection. The particles are labeled by a means which does not significantly affect the physical properties of the particles; for example, the particles are labeled internally (that is, the label is included within the particle, such as within the liposome or inside the polystyrene latex bead). Representative labels include luminescent labels; chemiluminescent labels; phosphorescent labels; enzyme-linked labels; chemical labels, such as electroactive agents (e.g., ferrocyanide); and colorimetric labels, such as dyes or fluorescent labels. In one embodiment, a fluorescent label is used. In another embodiment, phosphorescent particles are used, particularly "up-converting" phosphorescent particles, such as those described in U.S. Pat. No. 5,043,265.

The particles are coated with an analyte binding agent that is a second member of the binding pair. As described above, the analyte binding agent (second member of the binding pair) specifically and preferentially binds to the analyte of interest (fast member of the binding pair). Representative analyte binding agents include antibodies (or fragments thereof); haptens; drug conjugates; receptors; or other binding partners. In one preferred embodiment, the analyte binding agent is an antibody to the analyte of interest. Antibodies can be monoclonal antibodies or polyclonal antibodies. The term "antibody", as used herein, also refers to antibody fragments which are sufficient to bind to the analyte of interest.

Alternatively, in another embodiment, molecules which specifically bind to the analyte of interest, such as engineered proteins having analyte binding sites, can also be used; See (Holliger, P. and H. R. Hoogenbloom, *Trends in Biotechnology* 13:7–9 (1995) and Chamow, S. M. and A. Ashkenazi, *Trends in Biotechnology* 14:52–60 (1996)). In still another embodiment, if the analyte of interest is a drug, a hapten or other drug conjugate can be used as the analyte binding agent. Alternatively, in a further embodiment, a receptor which binds to the analyte can be used (e.g., if the analyte of interest is a ligand). If the analyte is an antibody of known specificity, the particles can be coated with the antigen against which the analyte-antibody is directed, or can be coated with antibody to the analyte-antibody. Furthermore, because the analyte and the analyte binding agent form a binding pair, compounds or molecules described as representative analytes can also serve as analyte binding agents, and those described as representative analyte binding agents can similarly serve as analytes, as described herein.

The analyte binding particles contained within the sample collection apparatus are stored in a stable form within the sample collection apparatus. A "stable form," as the term is used herein, indicates a form in which the particles do not significantly change in chemical makeup or physical state during storage. The stable form can be a liquid, gel, or solid form. In preferred embodiments, the analyte binding particles contained within the sample collection apparatus are evaporatively dried; freeze-dried; and/or vacuum-dried. Referring to FIG. 6, the analyte binding particles and analyte binding agents complex 160 is dried upon the mixing element 156, one suitable location being upon the lattice 154 of the paddle 108. Alternately, the analyte binding particles and analyte binding agents complex 260 is adhered to a wall of the sample well 204 as shown in the alternate embodiment of FIG. 9.

Figure 5:
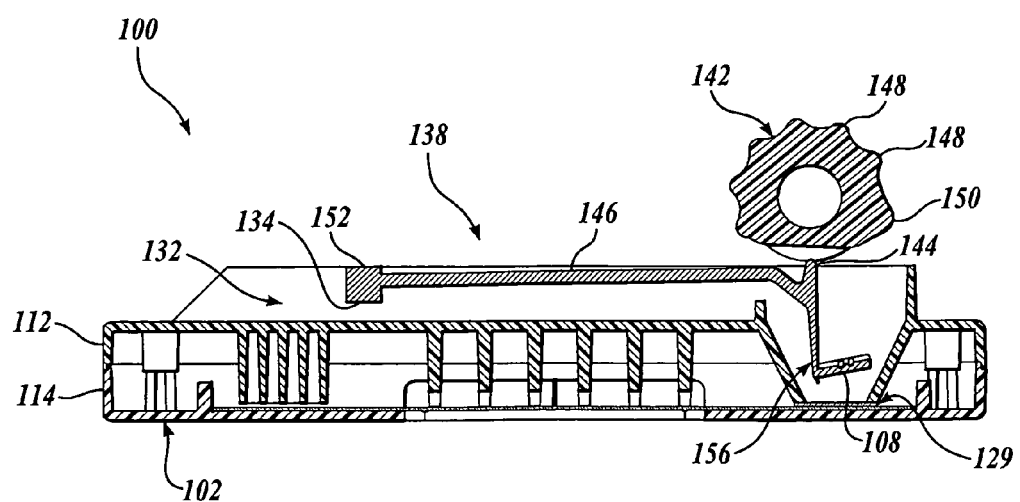
FIG. 5 is a cross-sectional view of the sample testing apparatus of FIG. 4, the cross-sectional cut taken substantially through Section 5—5 of FIG. 4.

Referring to FIG. 1, to perform the assay, a fluid sample to be assessed for the presence of the analyte of interest, as described above, is used. In one embodiment, the fluid sample is introduced into (drawn into, poured into, or otherwise placed into) the sample wells 104. For example, in one embodiment, the fluid sample is discharged into the sample wells 104 by a well known sampling instrument (not shown). Referring to FIG. 6, the shaft 140 of the mixing system 106 is rotated in the direction of arrow 162, from the position of the shaft 140 as shown in FIG. 5, causing the mixing lobes 148 to engage the cam followers 144. This results in the mixing paddles 108 reciprocating within the sample wells 104. The motion of the mixing paddles 108 causes the mixing of the fluid samples 105 with the analyte binding particles and analyte binding agent complexes 160, forming a "mixed fluid sample." If the analyte binding particles are evaporatively-, freeze- or vacuum-dried, the introduction and mixing of the fluid samples 105 within the sample wells 104 results in rehydration and suspension of the analyte binding particles and analyte binding agent complexes 160 in the fluid samples 105.

The fluid sample 105 may further include a buffer (e.g., for dilution) forming a "buffered, mixed fluid sample." Preferably, the buffer is added and mixed with the fluid sample 105 prior to introducing the fluid sample into the sample well 104. If the analyte of interest is a solid (e.g., a powder, a particulate; spore; or other particle, as described above), the fluid sample as described above can be prepared by introducing the solid into a buffer container having a buffer solution therein. In this embodiment, the buffered, mixed fluid sample is formed by introducing the fluid sample (comprising the buffer) into the sample well. In another embodiment, the buffer is introduced into the sample well, followed by introduction of the fluid sample into the sample well. In yet another embodiment, the fluid sample is introduced into the sample well, followed by introduction of the buffer into the sample well.

The buffer can be an aqueous fluid that supports a reaction between the analyte of interest and the analyte binding agent (e.g., does not interfere with antibody/antigen interaction); and that has a viscosity that is sufficiently low to allow movement of the fluid by capillary action. In one embodiment, the buffer contains one or more of the following components: a buffering agent (e.g., phosphate); a salt (e.g., NaCl); a protein stabilizer (e.g., BSA, casein, serum); and/or a detergent such as a nonionic detergent or a surfactant (e.g., one or more of the following agents commonly available in surfactant tool kits: NINATE411, Zonyl FSN 100, Aerosol OT 100%, GEROPON T-77, BIO-TERGE AS-40, STANDAPOL ES-1, Tetronic 1307, Surfnyol 465, Surfynol 485, Surfynol 104PG-50, IGEPAL, CA210, TRITON X-45, TRITON X-100, TRITON X305, SILWET L7600, RHODASURF ON-870, Cremophor EL, TWEEN 20, TWEEN 80, BRIJ 35, CHEMAL LA-9, Pluronic L64, SURFACTANT 10G, SPAN 60, CREL). Optionally, if desired, the buffer can contain a thickening agent. Such components for buffers are commercially available. Representative buffers include, for example, saline, or 50 mM Tris-HCl, pH 7.2. Alternatively, water can be used in lieu of a buffered solution; as used herein, the term "buffer" refers to either a buffered solution or to water.

Referring to FIG. 6, in a preferred embodiment, the analyte binding particles and analyte binding agent complex 160 is disposed in the sample well 104, such as upon the mixing paddle 108. Placing of the fluid sample in the sample well 104 results in the rehydration of the dried analyte binding particles and forming a mixed fluid sample. If the analyte of interest is present in the buffered, mixed fluid sample, binding occurs between the analyte and the analyte binding particles. "Binding" of analyte to the analyte binding particles indicates that the analyte binding agent coated onto the particle is interacting with (e.g., binding to) analyte of interest. Analyte binding particles which have been maintained (incubated) under conditions allowing analyte in the fluid (if present) to bind to the analyte binding particles immobilized in the contact region are referred to herein as "contacted analyte binding particles". Contacted analyte binding particles may or may not have analyte bound to the analyte binding agent, depending on whether or not analyte is present in the fluid sample and whether analyte has bound to the analyte binding agent on the analyte binding particles.

Because there are multiple binding sites for analyte on the analyte binding particles, the presence and the concentration of analyte bound to analyte binding particles varies; the concentration of analyte bound to the analyte binding particles increases proportionally with the amount of analyte present in the fluid sample, and the probability of an analyte binding particle being arrested in the sample capture zone (as described below) similarly increases with increasing amount of analyte bound to the analyte binding particles. Thus, the population of contacted analyte binding particles may comprise particles having various amount of analyte bound to the analyte binding agent, as well as particles having no analyte bound to the analyte binding agent (just as the analyte binding particles initially have no analyte bound to the analyte binding agent). Furthermore, the degree of binding increases as the time factor of the conditions increases: while the majority of binding occurs within one minute and preferably less than 60 seconds, additional incubation (e.g., more than one minute) may result in additional binding.

Referring to FIG. 7, the buffered, mixed fluid sample is applied to the application point of the membrane strip 118 of the solid phase apparatus, or to the application pad, if present, after the fluid sample is mixed for a selected duration in the sample well 104. The duration of mixing affects the characteristics of the reaction (sensitivity and accuracy) and is controllable. Thus, by selectively adjusting the duration of mixing by controlling when the valve 129 is opened, a user may selectively control the sensitivity and accuracy of the assay. In one working embodiment, the fluid sample is mixed for a time of about 30 seconds to about 1 minute, although it should be apparent to those skilled in the art that mixing durations of longer or shorter periods are suitable for use with the present invention.

The configuring of the valve in the open position to release the fluid sample is accomplished by rotation of the shaft 140 in the direction of arrow 162 such that the puncture lobe 150 engages the cam follower 144. The increased height of the puncture lobe 150 increases the displacement of the mixing element 156. This results in the spike 158 piercing/puncturing the barrier 130, causing an aperture to be formed therein. Upon further rotation of the shaft 140, the spike 158 is lifted from the barrier 130 as the puncture lobe 150 rotates past the cam follower 144. As the spike 158 lifts out of the aperture, the fluid sample flows from the sample well 104 and onto the membrane strip 118.

After the membrane strip 118 is contacted with the buffered, mixed fluid sample, the membrane strip 118 is maintained under conditions which allow fluid to move by capillary action to and through the membrane strip 118. The contacted analyte binding particles move through the membrane strip 118 as a result of capillary action of the fluid from the buffered, mixed fluid sample, and the contacted analyte binding particles move along the membrane strip 118 to and through the "sample capture zone" on the membrane and subsequently to and through the "control capture zone." The membrane strip 118 is maintained under conditions (e.g., sufficient time and fluid volume) which allow the contacted analyte binding particles to move by capillary action along the membrane to and through the sample capture zone and subsequently to the control capture zone, and subsequently beyond the capture zones (e.g., into a wicking pad), thereby removing any non-bound particles from the capture zones.

The movement of some of the contacted analyte binding particles is arrested by binding of contacted analyte binding particles to the sample capture reagent 164 in the sample capture zone and subsequently by binding of some of the contacted analyte binding particles to the control capture reagent in the control capture zone. In one preferred embodiment, the analyte binding agent is an antibody to the antigen of interest, and the control capture reagent can be an antibody against immunoglobulin of the species from which the analyte binding agent is derived. In this embodiment, the antibody to immunoglobulin should be non-cross reactive with other components of the sample: for example, if a human sample is being tested, an antibody that does not react with human immunoglobulin can be used as the control capture reagent. In another embodiment, the analyte binding agent is operable not to bind directly with the antigen of interest as described above, but instead bind to another unrelated material such as a protein associated with the antigen of interest.

Sample capture reagent binds to contacted analyte binding particles by binding to analyte which is bound to analyte binding agent on the contacted analyte binding particles. The term, "sample-reagent-particle complexes", as used herein, refers to a complex of the sample capture reagent 164 and contacted analyte binding particles. Contacted analyte binding particles are arrested in the sample capture zone, forming the sample-reagent-particle complexes, due to capture of contacted analyte binding particles by interaction of analyte with sample capture reagent 164 in the sample capture zone.

Control capture reagent 164 binds to contacted analyte binding particles by binding to analyte binding agent on the contacted analyte binding particles. The term, "control-reagent-particle complexes," as used herein, refers to a complex of the control capture reagent and contacted analyte binding particles. Contacted analyte binding particles are arrested in the control capture zone, forming the control-reagent-particle complexes, due to capture of contacted analyte binding particles by interaction of analyte binding particles with control capture reagent in the control capture zone. As indicated above, the control capture reagent interacts with the analyte binding particles (e.g., with the analyte binding agent on the analyte binding agent-coated particles, or another material on the particles, or with the particles themselves), but not with the analyte itself.

Capillary action subsequently moves any contacted analyte binding particles that have not been arrested in either the sample capture zone or the control capture zone, onwards beyond these zones, thereby removing any particles that have not been arrested. In a preferred embodiment, the fluid moves any contacted analyte binding particles that have not been arrested, into a wicking pad which follows the control capture zone.

If desired, a secondary wash step can be used. A buffer (e.g., the buffer described above) can be applied at the application point after the buffered, mixed fluid sample has soaked in to the membrane strip or into the application pad, if present. The secondary wash step can be used at any time thereafter, provided that it does not dilute the buffered, mixed fluid sample. A secondary wash step can contribute to reduction of background signal when the analyte binding particles are detected, as described below.

The amount of analyte binding particles arrested in the sample capture zone (sample-reagent-particle complexes) is then detected using an appropriate means for the type of label used on the analyte binding particles. In a preferred embodiment, the amount is detected by an optical method, such as by measuring the amount of fluorescence of the label of the analyte binding particles. Alternatively, the amount of sample-reagent-particle complexes can be detected using electrical conductivity or dielectric (capacitance). Alternatively, electrochemical detection of released electroactive agents, such as indium, bismuth, gallium or tellurium ions, as described by Hayes et al. (*Analytical Chem.* 66:1860–1865 (1994)) or ferrocyanide as suggested by Roberts and Durst (*Analytical Chem.* 67:482–491 (1995)) can be used. For example, if liposomes are used, ferrocyanide encapsulated within the liposome can be released by addition of a drop of detergent at the capture zone, and the released ferrocyanide detected electrochemically (Roberts and Durst, id.). If chelating agent-protein conjugates are used to chelate metal ions, addition of a drop of acid at the capture zone will release the ions and allow quantitation by anodic stripping voltametry (Hayes et al., id.). Similarly, the amount of analyte binding particles arrested in the control capture zone is detected in the same manner as the amount of analyte binding particles in the sample capture zone.

In one embodiment, the detected amount of analyte binding particles is represented by a curve that is directly related to the amount of label present at positions along the solid phase (e.g., the membrane strip). For example, the detected amounts of particles at each position on the membrane strip (e.g., at the sample capture zone and the control capture zone, and/or areas in between or adjacent to the sample capture zone and the control capture zone, and/or other areas of the membrane strip) can be determined and plotted as a function of the distance of the position along the membrane strip. The amount of particles can then be calculated as a function of the area under the curve, which is related to the amount of label present.

A corrected analyte binding particle amount is then determined, and the amount of analyte can then be determined from the corrected analyte binding particle amount using appropriate calculations. The corrected analyte binding particle amount is based on the amount of analyte binding particles arrested in the sample capture zone and in the control capture zone. For example, in one embodiment, the corrected analyte binding particle amount is determined as a ratio (R) of the analyte binding particle amount present in the sample capture zone to the analyte binding particle amount present in the control capture zone. The amount of analyte present can be then determined from the corrected analyte binding particle amount (the ratio), utilizing a standard curve. The standard curve is generated by preparing a series of control samples, containing known concentrations of the analyte of interest in the fluid in which the analyte is to be detected (for example, such as serum depleted of the analyte). The assay is then performed on the series of control samples; the value of R is measured for each control sample; and the R values are plotted as a function of the concentration of analyte included in the control sample. Samples containing an unknown amount of analyte (the "test samples") are assayed by measuring the value of R for the test sample, and the concentration of analyte in the test sample is determined by referring to the standard curve. As above, one standard curve can be generated and used for all test samples in a lot (e.g., for all test samples using a specified preparation of test reagents); it is not necessary that the standard curve be re-generated for each test sample. In another embodiment, the corrected analyte binding particle amount is determined as a ratio (R) of the amount of the analyte binding particle amount present in the sample capture zone, to the sum of the analyte binding particle amount present in the control capture zone and the analyte binding particle amount present in the sample capture zone. The amount of analyte present can be then determined from corrected analyte binding particle amount (the ratio), utilizing a standard curve. Alternatively, other ratios and/or standard curves can also be used to determine the amount of analyte in the sample. In addition, if desired, the amount of label that is present in the background can be subtracted from the analyte binding particle amount present in the sample capture zone and the analyte binding particle amount present in the control capture zone prior to calculation of the ratio (R).

"Competitive" or "Inhibition" Assays

The "competitive" or "inhibition" assay of the invention, like the "sandwich" assays, utilizes a solid phase apparatus including a membrane strip, as described above, that includes an application point, a sample capture zone, and a control capture zone. The membrane strip may optionally include a wicking pad following the control capture zone, and a sample pad preceding the application point. As before, the "application point" is the position on the membrane where a fluid sample is applied. This embodiment also utilizes the sample testing apparatus as described above. The sample testing apparatus for the competitive (inhibition) assay contains in the sample well a population of "analyte coated particles" which are coated with the analyte of interest (in lieu of being coated with an analyte binding agent, as described for the "sandwich" assays) or with an analog of the analyte of interest. An "analog" of the analyte, as used herein, is a compound that has similar binding characteristics as the analyte, in that it forms a binding pair with the analyte-binding agent as described above. The analyte or analog of the analyte can be coated directly on the particles, or can be indirectly bound to the particles. As used below, the term "analyte coated particles" can refer to particles that are coated either with an analyte of interest or with an analog of the analyte of interest. As above with regard to the sandwich assay, the population of particles varies, depending on the size and composition of the particles, the composition of the membrane of the solid phase apparatus, and the level of sensitivity of the assay.

As above, the sample capture zone refers to a point on the membrane strip at which a sample capture reagent is immobilized. The sample capture reagent is an analyte binding agent, such as those described above. The sample capture reagent need not be the same analyte binding agent as described above; however, the sample capture reagent also forms a binding pair with the analyte of interest, in that it specifically and preferentially binds to the analyte of interest. As above, in a preferred embodiment, the sample capture reagent is an antibody directed against the analyte; it can be directed against the same epitope of the analyte as, or against a different epitope of the analyte form, the epitope that binds to the antibodies used as analyte binding agents coated on the particles.

The apparatus additionally includes a control capture reagent, as described above, that reacts with the analyte coated particles, but does not interact with the analyte to be measured: for example, the control capture reagent can react with another material on the particles (e.g., a carrier for the analyte that is bound to the particles; an antibody); or with the particles themselves. In a preferred embodiment, the sample capture reagent and the control capture agent are both antibodies. The control capture reagent is immobilized on the membrane (coated on and/or permeated in the membrane) in the control capture zone.

The components of the competitive assay are positioned in a similar manner as described above with regard to the "sandwich" assay. For example, in a preferred embodiment, the control capture zone is closely adjacent to the sample capture zone, so that the dynamics of the capillary action of the components of the assay are similar (e.g., essentially the same) at both the control capture zone and the sample capture zone; and yet the control capture zone and the sample capture zone are also sufficiently spaced such that the particles arrested in each zone can be quantitated individually. Furthermore, in a preferred embodiment, the sample capture zone is separated from the application point by a space that is a large distance, relative to the small distance between the sample capture zone and the control capture zone, in order to ensure that the speed of the capillary front is sufficiently slow to allow capture of particles, and the total time of migration is sufficiently long to allow for binding of analyte to the sample capture reagent.

To perform the competitive assay, a fluid sample to be assessed for the presence of the analyte of interest, as described above, is used. In one embodiment, the fluid sample is introduced into (drawn into, poured into, or otherwise placed into) the sample wells 104. Introduction of the fluid sample into the sample wells and mixing through the use of the mixing system 106 results in mixing of the fluid sample with the analyte coated particles, forming a "mixed fluid sample." Preferably, the analyte coated particles are evaporatively-, freeze- or vacuum-dried within the sample wells such that the introduction of the fluid sample into the sample well can result in rehydration and suspension of the analyte binding particles in the fluid sample.

The fluid sample may include a buffer (e.g., as described above), forming a "buffered, mixed fluid sample." The buffered, mixed fluid sample may be formed in any number of ways, including mixing the buffer with the fluid sample prior to placing the fluid sample into the sample well, or by introducing the buffer into the sample well prior to introducing the fluid sample. Alternatively, if the analyte of interest is a solid (e.g., a powder, a particulate; spore; or other particle, as described above), the fluid sample as described above can be prepared by mixing the solid with the buffer. In this embodiment, the buffered, mixed fluid sample is formed by introducing the fluid sample (comprising the buffer) into the sample well.

The buffered, mixed fluid sample is applied to the application point of the membrane strip 118 of the solid phase apparatus, or to the application pad, if present. After the membrane strip 118 is contacted with the buffered, mixed fluid sample, the membrane strip 118 is maintained under conditions which allow fluid to move by capillary action to and through the membrane strip 118. The analyte coated particles (and analyte, if present in the sample) move through the membrane as a result of capillary action of the fluid from the buffered, mixed fluid sample, to and through the "sample capture zone" on the membrane and subsequently to and through the "control capture zone." The membrane strip is maintained under conditions (e.g., sufficient time and fluid volume) which allow the analyte coated particles to move by capillary action along the membrane to and through the sample capture zone and subsequently to the control capture zone, and subsequently beyond the capture zones (e.g., into a wicking pad), thereby removing any non-bound particles from the capture zones.

The movement of some of the analyte coated particles is arrested by binding of analyte coated particles to the sample capture reagent in the sample capture zone, and subsequently by binding of some of the analyze coated particles to the control capture reagent in the control capture zone. The analyte coated particles compete with analyte (if present) in the sample for binding to the sample capture reagent. The sample capture reagent binds to analyte coated particles by binding to analyte on the analyte coated particles. The term, "sample-reagent-analyte-coated-particle complexes", as used herein, refers to a complex of the sample capture reagent and analyte coated particles. The analyte coated particles are arrested in the sample capture zone, forming the sample-reagent-analyte-coated-particle complexes, due to capture of the analyte coated particles by interaction of the analyte on the particles with the sample capture reagent in the sample capture zone.

The control capture reagent binds to analyte coated particles by binding to any component of the analyte-coated particles except the analyte itself. The term, "control-reagent-analyte-coated particle complexes," as used above, refers to a complex of the control capture reagent and analyte coated particles. As above, the analyte coated particles are arrested in the control capture zone, forming the control-reagent-analyte-coated particle complexes, due to capture of the analyte coated particles by interaction of the analyte binding particles with the control capture reagent in the control capture zone.

Capillary action subsequently moves any analyte coated particles that have not been arrested in either the sample capture zone or the control capture zone, onwards beyond the control capture zone. In a preferred embodiment, the fluid moves any contacted analyte coated particles that have not been arrested in either capture-zone into a wicking pad which follows the control capture zone.

The amount of analyte coated particles arrested in the sample capture zone is then detected. The analyte coated particles are detected using an appropriate means for the type of label used on the analyte coated particles. In a preferred embodiment, the amount of analyte coated particles is detected by an optical method, such as by measuring the amount of fluorescence of the label of the analyte-binding particles. The amount of analyte coated particles arrested in the control capture zone is detected in the same manner as the amount of analyte coated particles in the sample capture zone. In one embodiment, as described above, the amount of analyte coated particles is represented by a curve that is directly related to the amount of label present at positions along the solid phase (e.g., the membrane strip). For example, the amount of particles at each position on the membrane strip (e.g., at the sample capture zone and the control capture zone, and/or areas in between or adjacent to the sample capture zone and the control capture zone, and/or other areas of the membrane strip) can be determined and plotted as a function of the distance of the position along the membrane strip. The amount of particles can then be calculated as a function of the area under the curve, which is related to the amount of label present.

A corrected analyte coated particle amount is determined, and the amount of analyte can then be determined from the corrected analyte coated particle amount using appropriate calculations. The corrected analyte coated particle amount is based on the amount of analyte coated particles arrested in the sample capture zone and in the control capture zone. For example, in one embodiment, the corrected analyte coated-particle amount is inversely proportional to a ratio (R) of the analyte-coated particle amount present in the sample capture zone to the analyte-coated particle amount present in the control capture zone. The amount of analyte present can be then determined from the corrected analyte coated particle amount (the ratio), utilizing a standard curve. The standard curve is generated by preparing a series of control samples, containing known concentrations of the analyte of interest in the fluid in which the analyte is to be detected (such as serum depleted of the analyte). The assay is then performed on the series of control samples; the value of R is measured for each control sample; and the R values are plotted as a function of the concentration of analyte included inn the control sample. Samples containing an unknown amount of analyte (the "test samples") are assayed by measuring the value of R for the test sample, and the concentration of analyte in the test sample is determined by referring to the standard curve. As above, one standard curve can be generated and used for all test samples in a lot (e.g., for all test samples using a specified preparation of test reagents); it is not necessary that the standard curve be regenerated for each test sample. In another embodiment, the corrected analyte coated particle amount is inversely proportional to a ratio (R) of the amount of the analyte coated particle amount present in the sample capture zone, to the sum of the analyte coated particle amount present in the control capture zone and the analyte coated particle amount present in the sample capture zone. The amount of analyte present can be then determined from corrected analyte coated particle amount (the ratio), utilizing a standard curve. Alternatively, other ratios and/or standard curves can also be used to determine the amount of analyte in the sample. In addition, if desired, the amount of label that is present in the background can be subtracted from the analyte coated particle amount present in the sample capture zone and the analyte coated particle amount present in the control capture zone prior to calculation of the ratio (R).

Benefits of the Invention

The methods of the invention provide assays with enhanced sensitivity, when compared with assays in which the analyte binding particles are imbedded within the membrane of the solid phase apparatus. In addition, because the analyte binding particles (or analyte coated particles) are dispersed in the buffered, mixed fluid sample prior to application of the buffered, mixed fluid sample to the solid phase membrane, the particles pass over the capture zone(s) in a continuous manner through the capillary action of the fluid, rather than in a quick wave on the crest of a fluid front.

Further, by placing the analyte binding particles and analyte binding agents complex 160 directly in the sample well 104, the testing process is streamlined, eliminating the need to have a user mix the sample with the analyte binding particles and analyte binding agents complex 160 prior to placing the fluid sample into the test well 104. The streamlining of the process eliminates the need for human intervention, such as the pipette mixing of the fluid sample with the analyte binding particles and analyte binding agents complex 160, making the illustrated embodiment of the sample testing apparatus 100 ideally suited for automated testing devices.

Alternate Embodiments

Although the assays of the invention have been described particularly in relation to immunoassays, the assays can similarly be used with other binding pairs as described above (e.g., nucleic acids, receptor-ligands, lectin-sugars), using the same methods as described above with the desired components as the analyte and the analyte binding agent.

Figure 9:
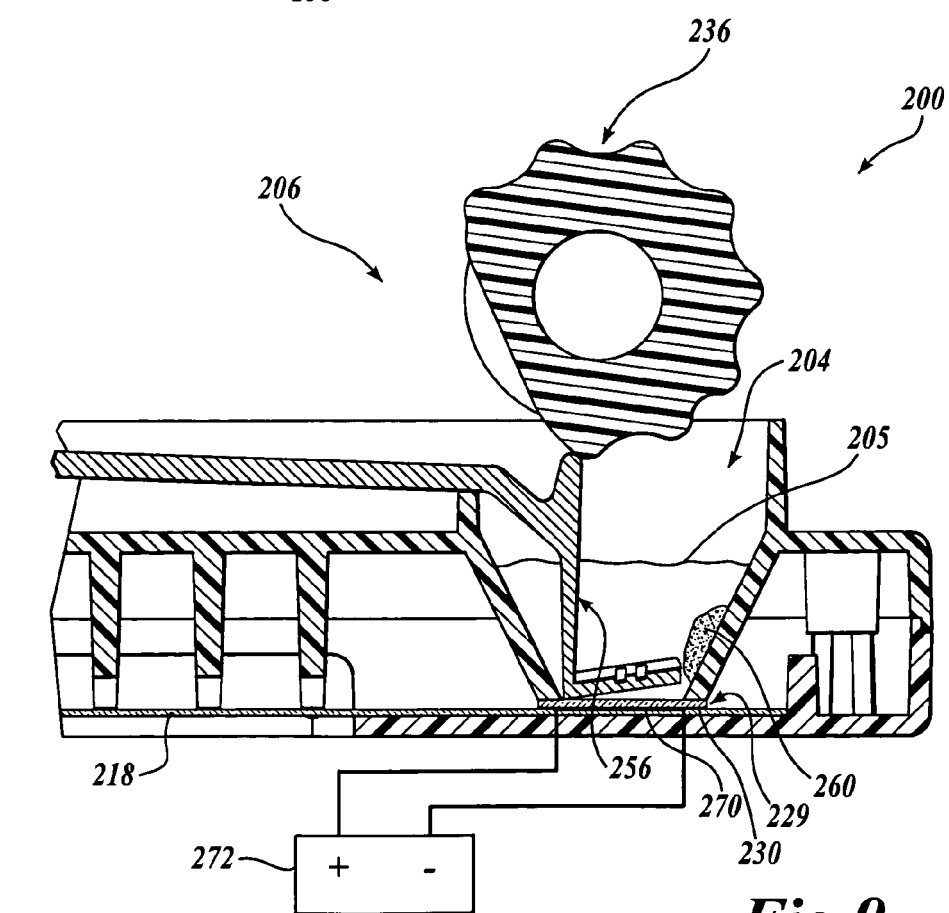
FIG. 9 is a cross-sectional view of an alternate embodiment of a sample testing apparatus formed in accordance with the present invention.

Turning to FIG. 9, an alternate embodiment of a sample testing apparatus 200 formed in accordance with the present invention is depicted. The sample testing apparatus 200 is substantially similar in operation and construction relative to the above described embodiment. Therefore, for the sake of brevity, this detailed description will focus only upon wherein the operation and construction deviates from that described above.

The sample testing apparatus 200 of FIG. 9 deviates from the previous embodiment in both the design of the valve 229 and of the mixing system 206. With regard to the valve 229, the valve of this embodiment also includes a barrier 230. However, the barrier 230 of this embodiment is adapted to form an aperture for releasing the sample 205 upon the membrane strip 218 by means other than puncture by the mixing element 256. For instant, in one embodiment, the barrier 230 is designed to begin dissolving upon contact by the sample. As the sample 205 is mixed in the sample well 204, the sample contacts the barrier 230, dissolving same until an aperture in the barrier 230 is formed and the sample is released upon the membrane strip 218. The material for use in the barrier 230 is preferably relatively inert to impede interfering with the testing, and is selected to resist dissolving for a selected duration such that sufficient mixing can occur before sample release, but dissolve soon enough to permit rapid testing. In one working embodiment, a sugar solution was disposed upon a screen framework and subsequently dried to form the barrier 230, wherein the concentration of the sugar in the solution was varied to adjust the duration that the barrier remained intact once in communication with the sample.

Still referring to FIG. 9, the barrier 230 may also be designed to be a meltable barrier 230. In this embodiment, a heating element 270 is disposed in heat transfer communication with the barrier 230. The heating element 270 is coupled to an electrical source, such as a battery 272. The electrical source selectively provides electricity to the heating element 270. When the electricity is applied to the heating element 270, the heating element is heated past its melting temperature. The barrier 230 subsequently melts, causing the release of the sample 205 contained within the sample well 204 upon the membrane strip 218.

Inasmuch as these alternative forms of the barrier 230 do not require puncture to release the sample, the mixing system 206 of this alternate embodiment has been modified. First, the mixing element 256 no longer requires the spike for puncturing the barrier 230. Second, the puncture lobe is also no longer required, and therefore has been removed in this alternate embodiment.

Figure 10:
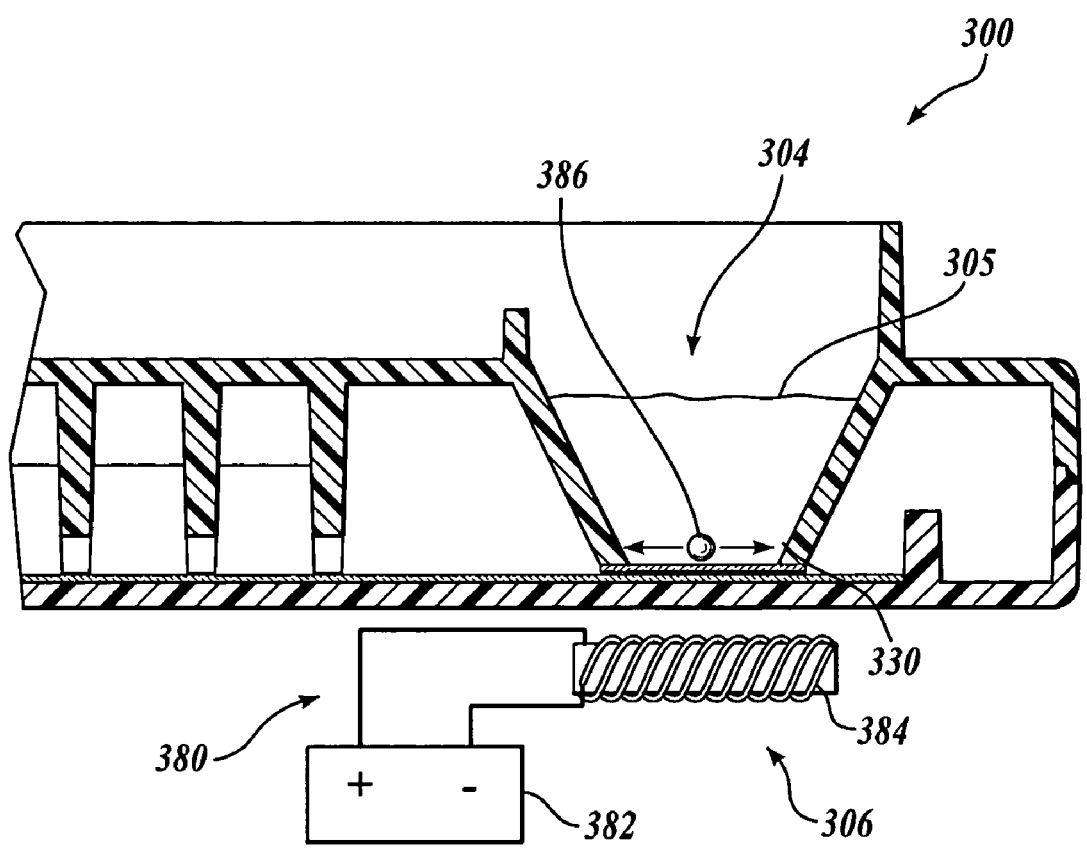
FIG. 10 is a cross-sectional elevation view of an alternate embodiment of the sample testing apparatus of FIG. 1 showing one embodiment of a magnetic based mixing system.

Turning to FIG. 10, another alternate embodiment of a sample testing apparatus 300 formed in accordance with the present invention is depicted. The sample testing apparatus 300 is substantially similar in operation and construction relative to the above described embodiments. Therefore, for the sake of brevity, this detailed description will focus only upon wherein the operation and construction deviates from that described above.

The sample testing apparatus 300 of FIG. 10 deviates from the previous embodiments in the design of the mixing system 306. The mixing system 306 of this embodiment is a magnetic based mixing system. Moreover, the mixing system 306 includes a magnetic field generating device 380 operable to generate a magnetic field. One suitable example of a magnetic field generating device 380 is an electromagnet wherein the magnetic field is generated by directing an electrical current produced by an energy source, such as a battery 382, through a coil of wire 384. The magnetic field can be switched on and off, or reversed, or its strength varied, by controlling the electric current through the coil of wire 384. The fluctuations in the magnetic field are used to move a mixing element 386 within the sample well 304, thereby mixing the fluid sample 305. The magnetic field may be controlled in such a manner that the mixing element 386 may be selectively driven down upon or through the barrier 330 to push open or puncture the barrier 330, resulting in the release of the fluid sample 305 from the sample well 304.

In the illustrated embodiment, the mixing element 386 is an iron sphere, however it should be apparent to those skilled in the art that the mixing element 386 may take the form of any shape and of any magnetic material able to interact with a magnetic field, one suitable example being a steel plate. Further, although the magnetic field is described as being varied in the illustrated embodiment to cause the magnetic mixing element 386 to move, it should be apparent to those skilled in the art that alternately, the magnetic field may be substantially constant, and the magnetic field generating device 380 moved to cause the mixing element 386 to correspondingly move.

Kits of the Invention

The invention also includes kits for use in the methods described herein. Kit components can include: first and/or second members of a specific binding pair, buffers and/or buffer containers, sample test apparatus, one or more solid phase apparatus (optionally comprising an application pad and/or wicking pad), control samples for generation of a standard curve and/or other standard curve information, analyte binding particles, analyte coated particles, and/or control particles, capture reagents, antibodies, tools to assist in collecting of samples to be assessed for analyte of interest (e.g., swabs), disposal apparatus (e.g., biohazard waste bags), and/or other information or instructions regarding the sample collection apparatus (e.g., lot information, expiration date, etc.). For example, in one embodiment, a kit comprises at least one sample testing apparatus having analyte binding particles disposed therein, such as analyte binding particles evaporatively-dried, vacuum-dried or freeze-dried in the sample well. In another embodiment, a kit comprises at least one solid phase apparatus as described herein and at least one sample testing apparatus. The embodiments can also optionally contain information regarding the standard curve, lot information, and/or expiration date relating to the analyte binding particles dispersed in the sample wells. In yet another preferred embodiment, a kit comprises at least one sample testing apparatus having dried analyte binding particles thereon; at least one solid phase apparatus; and at least one buffer container. This preferred embodiment can also optionally contain buffer within the buffer container.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A sample testing apparatus for use in quantitatively measuring an amount of an analyte in a fluid sample, comprising:
   (1) a plurality of separate sample wells arranged in a row, each for receiving a sample containing an analyte;
   (2) a quantity of solid analyte binding agent disposed in each of the sample wells;

(3) a mixing assembly having:
   (a) a plurality of mixing elements, including at least one paddle in each sample well for aiding in mixing of the sample with the solid analyte binding agent;
   (b) a rotary shaft extending lengthwise of the row of sample wells, said shaft having a plurality of peripheral lobes including a plurality of circumferentially spaced first and second peripheral cam lobes of different heights aligned with and engageable against each of the mixing elements;
(4) a barrier within each sample well normally impeding flow of the sample from the sample well, the mixing elements including puncture members aligned with the bafflers and moveable to puncture positions for penetrating the bafflers to provide apertures permitting discharge of samples from the sample wells;
(5) a biasing device for biasing the mixing elements from a second position to a first position within the sample wells; and
(6) an actuator assembly for rotating the rotary shaft such that at least the first cam lobes engage and move the mixing elements in the sample cells such that the paddles are selectively reciprocated back and forth between the first position and the second position for mixing the sample with the solid analyte binding agent, at least one of the second cam lobes for each of the sample wells and said puncture elements being constructed and arranged relatively such that selective rotary movement of the rotary shaft moves the puncture elements of the respective mixing elements to the puncture positions for penetration of the barriers by the puncture members.

* * * * *

UNITED STATES PATENT AND TRADEMARK OFFICE
CERTIFICATE OF CORRECTION

PATENT NO. : 7,056,473 B2
APPLICATION NO. : 10/834447
DATED : June 6, 2006
INVENTOR(S) : P.C. Harris et al.

It is certified that error appears in the above-identified patent and that said Letters Patent is hereby corrected as shown below:

| COLUMN | LINE | ERROR |
|---|---|---|
| 23 (Claim 1, | 15 line 21) | "bafflers" should read --barriers-- |
| 23 (Claim 1, | 16 line 22) | "bafflers" should read --barriers-- |

Signed and Sealed this

Third Day of July, 2007

JON W. DUDAS
*Director of the United States Patent and Trademark Office*